United States Patent [19]

Inomata et al.

[11] Patent Number: 5,087,722

[45] Date of Patent: Feb. 11, 1992

[54] PROCESS FOR PRODUCING NORCAMPHANE DICARBONITRILES

[75] Inventors: Masamitu Inomata; Naokazu Shiotani; Kazuo Koshizuka; Minato Karasawa, all of Chiba, Japan

[73] Assignee: Mitsui Toatsu Chemicals, Inc., Tokyo, Japan

[21] Appl. No.: 592,314

[22] Filed: Oct. 3, 1990

[30] Foreign Application Priority Data

Dec. 27, 1989 [JP] Japan ................... 1-336611

[51] Int. Cl.$^5$ .......................... C07C 253/10
[52] U.S. Cl. ................... 558/338; 558/428
[58] Field of Search .............. 558/338, 339, 428

[56] References Cited

U.S. PATENT DOCUMENTS

| | | | |
|---|---|---|---|
| 2,666,748 | 1/1954 | Arthur, Jr. et al. | 558/339 X |
| 2,666,780 | 1/1954 | Arthur, Jr. et al. | 558/339 |
| 3,328,443 | 6/1967 | Clark et al. | 260/439 |
| 3,496,217 | 2/1970 | Drinkard, Jr. et al. | 260/465.8 |
| 3,655,723 | 4/1972 | Drinkard, Jr. | 558/338 |
| 3,766,237 | 10/1973 | Chia et al. | 260/465.3 |
| 3,773,809 | 11/1973 | Walter | 558/338 |
| 3,775,461 | 11/1973 | Drinkard, Jr. et al. | 558/338 X |
| 3,818,068 | 6/1974 | Wells | 558/338 |
| 3,864,383 | 2/1975 | Fernholz et al. | 558/339 |
| 3,925,445 | 12/1975 | King et al. | 558/338 |
| 4,339,395 | 7/1982 | Barnette et al. | 558/338 |
| 4,385,007 | 5/1983 | Shook, Jr. | 558/338 |

FOREIGN PATENT DOCUMENTS 2212155 7/1989 United Kingdom .

OTHER PUBLICATIONS

J. Chem. Soc. London, (1960); pp. 1378–1389; Chatt, et al.
Am. Chem. Soc., 81, (1959); pp. 4200–4208; Merivethes et al.
Chem. Rev., 31, p. 319 (1942).
J. Chem. Soc. Chem. Commun, 1969, pp. 112–113, Brown et al.
Am. Chem. Soc. Div. Pet. Chem. Preprints 14, pp. B29–B34, (1969), Brown et al.
J. Am. Chem. Soc. 76, pp. 5364–5367; (1954); Arthur, Jr. et al.

*Primary Examiner*—Joseph Paul Brust
*Attorney, Agent, or Firm*—Burns, Doane, Swecker & Mathis

[57] ABSTRACT

A norcamphane dicarbonitrile is produced by hydrocyanation of bicyclo [2,2,1]-5-heptene-2-carbonitrile in the presence of a zerovalent nickel complex catalyst and Lewis acid and treating the resulting crude product by contact with a catalyst treating agent.

8 Claims, No Drawings

PROCESS FOR PRODUCING NORCAMPHANE DICARBONITRILES

BACKGROUND OF THE INVENTION

1. Field of the Invention The present invention relates to a process for producing a norcamphane dicarbonitrile (hereinafter referred to as ("NDC").

NDC's may be used as intermediates for organic synthesis. For example, NDC's can be used for producing useful diamines such as bis (aminomethyl) norcamphanes (hereinafter referred to as "BAN's") of general formula (y),

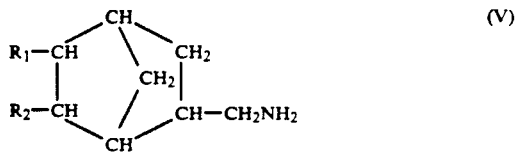

and $R_2$ are hydrogen or aminomethyl and RI and $R_2$ are different.

BAN's can be used directly as epoxy resin curing agents. They may be also used for producing polyamide resins by reaction with aliphatic dicarboxylic acids. Or, BAN's can be converted to diisocyanates by treating with phosgene. Diisocyanates are useful for various reactions.

2. Description of Related Art

In the past only two processes for producing NDC's by hydrocyanation of bicyclo [2,2,1[-5-heptene-2-carbonitrile (hereinafter referred to as "BHC") were known. (i) First, there is a process using a catalyst system comprising a cobalt carbonyl catalyst and triphenyl phosphine (see U.S. Pat. Nos. 2,666,780 and 2,666,748, and J. Am. Chem. Soc., 76, 5364 (1954)). In the other process (ii) a catalyst system is used which comprises tetrakis (triphenyl phosphite) palladium and triphenyl phosphite (see J. Chem. Soc. Chem. Commun., 1969, 112 and Am. Chem. Soc. Div. Pat. Chem. Preprints, 14, B29 (1969)).

Hydrocyanation of other substrate olefins is disclosed, for example, in U.S. Pat. No. 3,773,809. In that process (iii) there is a hydrocyanation of 3-pentenenitrile and 4-pentenenitrile in the presence of a catalyst system of a zerovalent nickel complex and triarylboron; and also involves extracting and isolating the remaining active catalyst components from the resulting crude product fluid and recirculating.

U.S. Pat. No. 3,818,068 discloses a process (iv) for removing a deactivated catalyst species from a crude product fluid similar to (iii) above.

In process (i) above, the cobalt catalyst and triphenyl phosphine are used in amounts of 31 wt. % and 15 wt. %, respectively, based On the substrate olefin, BHC. Hydrogen cyanide is used in an amount of 1.4 times the mole amount of BHC, and the yield of NDC's is 62% when the reaction is effected at 130° C. for 8 hours. In process (ii) above, an expensive palladium catalyst is used. Thus, the initial investment and running costs are high.

In process (iii) above, the amount of the catalysts is relatively large based on the substrate olefin subjected to hydrocyanation. Therefore, recovery and recirculation of the remaining active catalyst components are necessary.

In process (iv) above, in addition to recovery and recirculation of the active catalyst component as in process (iii), removing deactivated catalyst species is required. Effecting the procedures of (iii) and (iv) is complicated and a large investment cost is necessary.

Conventional processes have various problems, and a simple and economical process for producing NDC's is in demand.

SUMMARY OF THE INVENTION

It is an object of the present invention to provide a simple and economical process for producing an NDC. It is another object of the present invention to provide a process for producing an NDC with a relatively small amount of catalyst for hydrocyanation. It is a further object of the present invention to provide an NDC capable of providing a high yield of BAN's by a catalytic hydrogenation.

According to the present invention, there is provided a process for producing a norcamphane dicarbonitrile of general formula (II).

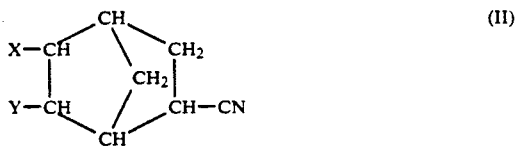

where X is hydrogen and Y is cyano, or X is cyano and Y is hydrogen. The process comprises hydrocyanating a bicyclo [2,2,1]-5-heptene-2-carbonitrile of the formula (I).

in the presence of a zerovalent nickel complex catalyst and a Lewis acid. Then, the resulting crude product is treated with a catalyst treating agent.

DESCRIPTION OF THE PREFERRED EMBODIMENTS

In view of the related art as mentioned above, the inventors carried out research on a highly active catalyst for hydrocyanation of BHC for the purpose of producing NDC's with high selectivity and good yield. They found that a catalyst system comprising a zerovalent nickel complex catalyst and a Lewis acid can produce NDC's with high selectivity and good yield. The results of their research is described in Japanese Patent Application No. 083970/1989 (hereinafter referred to as "JPA '970") and PCT/JP90/00450.

The Japanese Patent Application No.083970/1989 and the corresponding PCT/JP90/00450 are incorporated hereto by reference.

JPA '970 discloses a process for producing NDC's by hydrocyanating BHC in the presence of a zerovalent nickel complex catalyst such as tetrakis (triaryl phosphite) nickel, a neutral ligand such as triaryl phosphite and a Lewis acid such as zinc chloride, cadmium chloride, and tin chloride. A wide range of reaction conditions and relative amounts of the catalyst and the starting materials to be used in the hydrocyanation reaction, are also disclosed.

It was found that when the crude product fluid of NDC's produced by hydrocyanation according to JPA '970 is directly subjected to catalytic hydrogenation in the presence of an ordinary catalytic hydrogenation catalyst such as a Raney cobalt catalyst, Raney nickel catalyst, carried cobalt catalyst, platinum catalyst, rhodium catalyst, and ruthenium catalyst, the conversion of NDC's is lower than when highly purified NDC's are used, and the yield of BAN's, the end product, is low.

Therefore, the present inventors believed that a catalytic poison to the catalytic hydrogenation catalyst was present in the crude product fluid of NDC's after hydrocyanation. Therefore investigations were carried out to determine poison factors functioning as a catalytic poison to the catalytic hydrogenation catalyst contained in the crude product fluid of NDC's.

As a result, it has been determined that phosphites which are neutral ligands of the zerovalent nickel complex catalyst used as a catalyst for hydrocyanation and inorganic salts such as Lewis acids as promotors and the like, are the poison factors. In particular, it has been found that phosphites adversely affect the catalytic hydrogenation reaction of NDC's even in a small amount such as about 100 ppm based on NDC's.

It is believed that the unshared electron pair of the phosphorus atom in phosphites nucleophilically blocks the active surface of the catalytic hydrogenation catalyst. Therefore, working under the assumption that phosphites are a fatal poison factor to the catalytic hydrogenation catalyst, the inventors set out to develop effective methods for removing the phosphites.

First, removing phosphites by distillation, which was generally thought to be the simplest method, was tried. With this technique it was possible to remove trialkyl phosphites having lower alkyl groups, and low boiling points, and a large boiling point difference from the boiling point of NDC's (160°-70° C./3 mm Hg). However, in the case of triaryl phosphites, which are particularly preferable neutral ligands of a zerovalent nickel complex catalyst, for example, phosphites having boiling points distilling the NDC's is required. Further, in the case of phosphites having boiling points near that of NDC's, a large distillation column having many plates is necessary in addition to the severe condition.

The most troublesome problem with distillation is that even after completion of hydrocyanation, the catalysts remain in the crude product fluid of NDC's. When the fluid is subjected to distillation the catalysts precipitate as crystals and clog the distillation apparatus. The clogging significantly lowers the efficiency of the distillation operation. Thus, the yield becomes poor. Therefore, it was determined that the removal of phosphites by distillation was not able to be a useful method. Finally, the present inventors discovered that the crude product fluid of NDC's should be treated with a catalyst& treating agent by contacting the agent with the crude product fluid. When used in the catalytic hydrogenation reaction, the reaction is not hindered, but proceeds in the same way as when a purified NDC's of high purity is used, resulting in high yield of BAN's.

The zerovalent nickel complex catalyst used can be represented by the general formula (III), $$Ni [(A)(B)(C)(D)] \quad (III)$$

where A,B,C and D are, similar or dissimilar, and are neutral ligands represented by the general formula(IV), $$P (x)(y)(z) \quad (IV)$$

where P is phosphorus, x, y and z are similar or dissimilar, OR where R is selected from the group consisting of alkyl having 18 carbon atoms or less and aryl having 18 carbon atoms or less.

Exemplary suitable neutral ligands include triaryl phosphites such as triphenyl phosphite and the like; tri-substituted phenyl phosphite such as tri-halo substituted phenyl phosphite, tri-alkoxy substituted phenyl phosphite, tri-alkyl substituted phenyl phosphite; and trialkyl phosphites, and mixtures thereof.

Exemplary suitable tri-substituted phenyl phosphites include tri-m- or p-tolylphenyl phosphite, tri-m or p-chlorophenyl phosphite, tri-m or p-methoxyphenyl phosphite, and tri-m or p-nonylphenyl phosphite Exemplary suitable trialkyl phosphites include triethyl phosphite, triisopropyl phosphite, and tributyl phosphite One or more of the neutral ligands, A, B, C and D can leave the zerovalent nickel complex catalyst under most reaction conditions.

Exemplary suitable neutral ligands include triaryl phosphites and trialkyl phosphites, preferably triaryl phosphites, in particular, triphenyl phosphite, tri-m or p-tolylphenyl phosphite, and tri-m or p-nonylphenyl phosphite.

Exemplary suitable zerovalent nickel complex catalysts include tetrakis (triphenyl phosphite) nickel; tetrakis tri-substituted phenyl phosphite) nickel, for example, tetrakis (tri-halo-substituted phenyl phosphite) nickel tetrakis (tri-alkoxy-substituted phenyl phosphite) nickel and tetrakis (tri-alkyl-substituted phenyl phosphite) nickel; and tetrakis (trialkyl phosphite) nickel.

Exemplary suitable tetrakis (tri-substituted phenyl phosphite) nickels are tetrakis (tri-m or p-tolylphenyl phosphite) nickel tetrakis (tri-m or p-chlorophenyl phosphite) nickel, tetrakis (tri-m or p-methoxyphenyl phosphite) nickel, and tetrakis (tri-m or p-nonylphenyl phosphite) nickel.

Further suitable zerovalent nickel complex catalysts include tetrakis (trialkyl phosphite) nickel, for le, tetrakis (triethyl phosphite) nickel, tetrakis (triisopropyl phosphite) nickel, and tetrakis (tributyl phosphite) nickel.

In the present invention, it is preferable to carry out hydrocyanation in the presence of a neutral ligand so as to enhance the activity Of the zerovalent nickel complex catalyst and prolong the life of the catalyst.

Preparation of zerovalent nickel complex catalyst is disclosed, for example, in U.S. Pat. No. 3,328,448. J. Chem. Soc. London, 1378 (1960), J. Am. Chem. Soc., 81, 4200 (1959) and Inorg. Synth., 13, 108 or 112.

In the present invention, a Lewis acid is used as a promoter, and is, for example, a substance that can accept an electron pair.

Examples of Lewis acid are compounds composed of an anion and metallic cation selected from elements of groups II a, III a, IV a, V a, VI a, VII a, VIII, I b, II b, III b, and IV b of the periodic table.

Examples of the metallic cation are zinc, cadmium beryllium, aluminum, gallium, indium, silver, titanium, zirconium, hafnium, germanium, tin, vanadium, niobium, scandium, chromium, molybdenum, tungsten, manganese, rhenium, palladium, thorium, erbium, iron, cobalt, and boron ions.

Examples of anion are halogen anion such as chlorine, bromine, fluorine and iodine, anions of lower aliphatic acid of $C_2$–$C_7$, $HPO_3^{2-}$, $H_2PO_2^-$, $C_7F_{15}SO_3^-$, and $SO_4^{2-}$.

Particularly preferable metallic cations are zinc, cadmium, titanium, tin, vanadium, chromium, aluminum and boron ions.

Particularly preferable anions are chlorine ion, iodine ion, $HPO_3^{2-}$ and $H_2PO_2^-$.

In addition, other examples of a Lewis acid are organic boron, for example, trialkyl boron such as triethyl boron and triaryl boron such as triphenyl boron, and metal alkoxides such as aluminum isopropoxide and titanium isopropoxide Examples of preferable Lewis acid are zinc chloride, cadmium chloride, tin chloride, cadmium iodide, chromium chloride, boron trichloride, and triphenyl boron, and zinc chloride is particularly preferable.

The present invention will be explained further in detail below. In order to help to understand the present invention, the explanation is made referring to JPA '970 where catalysts for hydrocyanation are disclosed. That is, the explanation is given assuming that tetrakis (triphenyl phosphite) nickel ($NiL_4$ : L being a neutral ligand) is used as the zerovalent nickel complex catalyst, triphenyl phosphite (L : $P(OPh)_3$) as the neutral ligand, and zinc chloride ($ZnCl_2$) as the Lewis acid.

When the reaction is carried out according to the process of JPA '970 by using the above-mentioned catalyst system, the average composition of the crude product fluid of NDC's is as shown below.

| Ingredient | % by weight |
| --- | --- |
| $NiL_4$ | 0.0–2.0 |
| L:$P(OPh)_3$ | 0.40–8.0 |
| $ZnCl_2$ | 0.05–0.5 |
| BHC | 0.0–8.0 |
| NDC's | 80.0–98.5 |
| HCN | 0.0–0.10 |
| Others (including insoluble matters) | 0.10–4.0 |

The slight amount of hydrogen cyanide present in the crude product fluid of NDC's can be removed by passing nitrogen through the fluid. Further, insoluble matter from the deactivated catalyst system can be removed by filtration.

According to the present invention, the crude product fluid of NDC's, from which insoluble has been removed by filtration (hereinafter called "crude NDC's solution"), is treated by bringing the solution into contact with a catalyst treating agent.

The catalyst treating agent is an agent capable of acting on the catalysts (in particular, the above-mentioned phosphites) and easily removing them from the system, or capable of converting them to matter which does not behave as a catalytic poison to the catalytic hydrogenation catalyst.

Representative catalyst treating agents are an aqueous alkaline solution, an aqueous acidic solution, an oxidizing agent, and the like.

The aqueous alkaline solution may be any aqueous solution so long as the liquid exhibits alkalinity. Examples include aqueous solutions of alkaline metal hydroxides, aqueous solutions of alkaline earth metal hydroxides, aqueous solutions of alkaline metal carbonates, aqueous ammonia and the like.

The aqueous alkaline solution is preferably an aqueous solution of an alkaline metal hydroxide or an aqueous solution of an alkaline earth metal hydroxide. More preferably, it is an aqueous solution of sodium hydroxide, potassium hydroxide or barium hydroxide.

The aqueous acidic solution may be any aqueous solution so long as the liquid exhibits acidity. Examples include aqueous solutions of mineral acids, carboxylic acids and the like. Hydrochloric acid, sulfuric acid and acetic acid are preferred.

The oxidizing agents may be any oxidizing agents capable of donating oxygen. Examples include hydrogen peroxide, organic peroxides, organic peracids, sulfoxides, halogen, halogen compounds, ozone, nitrogen oxides, epoxides, amine-N-oxides, oxygen and the like. Preferably they are hydrogen peroxide, organic peroxides, sulfoxides, halogen, halogen compounds and oxygen.

More particularly, hydrogen peroxide may be used in the form of an aqueous solution, and an aqueous solution of alkyl hydroperoxide such as t-butyl hydroperoxide and the like can be used as an organic peroxide, dimethyl sulfoxide as a sulfoxide, aqueous halogen, aqueous hypohalites and the like as halogen and halogen compounds.

Oxygen can be used alone, and the action of oxygen can be accelerated by adding peroxides, radical initiators, such as 2,2'-arobis (isobutyronitrile), 2-hydroxy-2-methyl-1-phenylpropane-1-one and the like, and transition metal ions, and by irradiating with light. It is also possible to effect both the addition of the additives and the irradiation with light simultaneously.

When the catalyst treating agent is an aqueous alkaline solution or an acidic solution, the poisoning factor to the above-mentioned catalytic hydrogenation catalyst, i.e., phosphites (e.g. triphenyl phosphite) which are neutral ligands of zerovalent nickel complex catalysts for hydrocyanation, is hydrolyzed and converted to a water-soluble phosphite (e.g. phenyl phosphite or phosphorus acid and salts thereof).

Therefore, any aqueous solution in the alkaline or acidic pH range where hydrolysis of ordinary phosphites can proceed may be used. More particularly, an aqueous solution of pH 5.5 or less, or of pH 8.5 or higher may be used. Preferably it is an aqueous solution of pH 2 or less, or of pH 12 or higher.

The amount of aqueous alkaline or acidic solution is, in terms of the alkaline or acidic compound, 0.1–50 mol %, preferably 1–10 mol % based on NDC's. When it is less than 0.1 mol %, the treating effect is insufficient. On the other hand, when it is higher than 50 mol %, side reactions such as hydrolysis of cyano group of NDC's may proceed.

The aqueous alkaline or acidic solution can be contacted with the crude NDC's solution by mixing the two solutions in an agitation vessel with stirring. However, the contact may be effected by a continuous method using counter-current contact of the two solutions in a pipe.

In these contacting methods, the contacting temperature is usually 0–100° C., preferably 40°–80 ° C., and the contacting time may be appropriately set depending on the contacting method and contacting temperature, and is usually 5 hours or less, preferably 0.2–3.0 hours.

When the catalyst treating agent is an oxidizing agent, the function of the oxidizing agent is to oxidize phosphites (e.g. triphenyl phosphite) which are neutral ligands to phosphates (e.g. triphenyl phosphate), thereby rendering the phosphites nonpoisonous to the catalyst.

Among the phosphates produced by the oxidation, some lower trialkyl phosphates such as trimethyl, triethyl phosphates and the like are water-soluble, but triaryl phosphates (e.g. triphenyl phosphate) produced by oxidation of triaryl phosphites, which are particularly effective as neutral ligands for zerovalent nickel complex catalysts in the hydrocyanation reaction, are water-insoluble so that it is difficult to remove them from the system by washing with water.

However, the phosphates (e.g. triphenyl phosphate) are different from their corresponding phosphites (e.g. triphenyl phosphite) in properties and are not poison factors to catalysts of the catalytic hydrogenation reaction. Therefore, the phosphates may be carried in the starting materials for producing BAN's.

The amount of the oxidizing agent used usually ranges from 1 to 50 times mol based on phosphites contained in the crude NDC's solution.

As is clear from the above-mentioned mechanism of rendering the phosphites nonpoisonous, when the molar amount of oxidizing agent is less than the equimolar amount of phosphites (e.g. triphenyl phosphite), the full effect can not be expected. On the other hand, the upper limit of the amount of the oxidizing agent varies somewhat depending on the type of oxidizing agent and is not particularly critical. But when if exceeds 50 times the molar amount of phosphites, the effect does not increase and such a large amount is not preferable from an economical point of view. In addition, there can be side reactions. The amount is preferably 1-20 times mol. However, when the oxidizing agent is oxygen, the recovery is easy and the likelihood of side reactions is so little that the upper limit is not limited to the above-mentioned amount.

The method of contacting the crude NDC's solution with an oxidizing agent varies depending on the properties and characteristics of the oxidizing agent. When the oxidizing agent is present in the form of an aqueous solution, such as an aqueous hydrogen peroxide and an aqueous solution of alkylhydroperoxide, and is mixed with the crude NDC's solution, but a completely uniform solution can not be obtained, there is usually employed a method where the two liquids are mixed with stirring in an agitation vessel.

It is also possible to effect mixing using a continuous method of contacting the two liquids in a pipe in a countercurrent manner. When sulfoxides, epoxides and the like are used, they can be completely mixed with the Crude NDC's solution to give a uniform solution, and the contacting method offers no problem. In the case of using a gaseous oxidizing agent such as ozone, oxygen and the like, the contact may be carried out by an ordinary gas-liquid contacting method.

The contacting temperature varies somewhat depending upon the type of oxidizing agent and is usually −78 to 100° C., preferably 10° to 50° C.

The contacting time may be appropriately set depending on the type of oxidizing agent, contacting method and contacting temperature, and is usually 5 hours or less, preferably 0.2-3 hours.

According to the present invention, upon contacting the crude NDC's solution with a catalyst treating agent, it is possible to add an organic solvent to the crude NDC's solution to enhance fluidity of the crude NDC's solution.

According to the present invention, the crude NDC's solution is brought into contact with the catalyst treating agent to complete the steps of the present invention. As a result, for example, the catalytic hydrogenation reaction can proceed without any trouble, and therefore, the sufficient effect of the present invention can be confirmed.

However, when a hydrophobic organic solvent is added after treatment with a catalyst treating agent and then the organic phase is washed with water, the effect can be further ensured. It is not always necessary to add a hydrophobic organic solvent before washing with water, but the hydrophobic organic solvent accelerates the phase separation upon washing with water and therefore it is preferable to add it in advance.

Exemplary suitable hydrophobic organic solvents include aromatic hydrocarbons such as benzene, toluene, xylene and the like; aromatic halogenated hydrocarbons such as chlorobenzene, dichlorobenzene and the like; aliphatic ethers such as ethyl ether, isopropyl ether and the like; aliphatic halogenated hydrocarbons such as methylene chloride, chloroform, carbon tetrachloride, trichloroethane and the like; aliphatic alcohols having 4 carbon atoms or more such as n-butyl alcohol, isobutyl alcohol, n-amyl alcohol and the like; aliphatic carboxylic acid esters such as ethyl acetate, propyl acetate and the like; and aliphatic ketones such as methyl butyl ketone, methyl isobutyl ketone and the like. The hydrophobic organic solvents may be used alone or in combination. Preferable hydrophobic organic solvents are aromatic hydrocarbons such as benzene, toluene and the like.

The amount of hydrophobic organic solvent used is usually 0.05-20.0 parts by weight, preferably 0.5-5.0 parts by weight based on one part by weight of NDC's.

After adding a hydrophobic organic solvent, stirring and mixing, the resulting solution is allowed to stand so that the water phase can be separated from an organic phase. Then the water-soluble material is removed from the system (to the water phase) by washing the organic phase containing NDC's with water.

Various water-washing methods may be employed. Examples include a method comprising feeding the organic phase and water to an agitation vessel, stirring, mixing, allowing to stand and separating the water phase, and a method for separation by continuously contacting two liquids, i.e., an organic phase and water, in a pipe in a counter-current manner.

The amount of water used is usually 0.1-4 parts by weight, preferably 0.5-3 parts by weight per one part by weight of the organic phase containing NDC's. When the water amount is less than 0.1 part by weight, the effect of water-washing lowers gradually. On the other hand, when the water amount exceeds 4 parts by weight, the effect of water-washing does not substantially change and the amount of discharged water increases uneconomically.

An organic phase containing NDC's produced by the process of the present invention may be used as it is. Or the NDC's in the organic phase may be adjusted to an optional concentration by concentrating or diluting with an organic solvent, and then used for effecting the catalytic hydrogenation in the presence of an ordinary catalytic hydrogenation catalyst such as Raney cobalt catalyst, Raney nickel catalyst, carried cobalt catalyst, platinum catalyst, rhodium catalyst, ruthenium catalyst and the like. Thus, BAN's can be produced in high yield similar to the yield when a purified NDC's of high purity is used.

It is known that BHC's used in the present invention can be easily produced by Diels-Alder reaction of cyclopentadiene and acrylonitrile (Chem. Ber., 91, 1516 (1958); Chem. Rev., 31, 319 (1942)). Further, BHC's are usually available as a mixture of endo and exo isomers.

BHC's may be used at an optional isomer ratio and fur±her, each endo-form or exo-form of BHC may be used alone by isolating each isomer, for example, by distillation.

The present invention is a simple process comprising the hydrocyanation of BHC in the presence of a zerovalent nickel complex catalyst and a Lewis acid, and treating the resulting crude product fluid of NDC's with a catalyst treating agent. Further, the relative amount of the catalyst in the hydrocyanation is very small. Therefore, the process of the present invention is an excellent process for producing NDC's from an economical point of view.

In addition, as is clear from the following examples, the NDC's produced by the present invention can give useful diamines BAN's, in good yield by a catalytic hydrogenation reaction.

Therefore, the process for producing NDC's according to the present invention is a very advantageous commercial process.

The invention is now particularly described with reference to the following examples which are for the purpose of illustration only and are intended to imply no limitation thereon.

EXAMPLE 1

Preparation of Solution of Crude NDC's

A 300 ml. separable flask fitted with a stirrer, a thermometer, a gas inlet tube and a cooler was charged with BHC 239.4 g (2.00 mol), tetrakis (triphenyl phosphite) nickel, Ni(P(OPh)$_3$)$_4$, 2.48 g (1.91 m mol), zinc chloride 0.27 g (2.0 m mol) and triphenyl phosphite, p(Oph)$_3$, 2.48 g (7.99 m mol) and purged with nitrogen gas, and the temperature of the reactor gas elevated to 85° C. with stirring to dissolve the catalyst and others.

Then a nitrogen gas was introduced into a receiving vessel containing liquid hydrogen cyanide cooled with ice water and was bubbled through the reaction mixture to feed gaseous hydrogen cyanide together with nitrogen gas thereto and to effect a hydrogen cyanide addition reaction at 85° C. for 5 hours resulting in consumption of 56.8 g (2.10 mol) of hydrogen cyanide.

Further the same reaction procedure using the same starting materials and catalysts was repeated. In total, the reaction was carried out three times.

The crude NDC's product fluid obtained by the three reactions were mixed and subjected to analysis by means of gas chromatography, high performance liquid chromatography and atomic absorption spectrometry. The result of the analysis is as shown below. The total amount of the three crude NDC's product fluid was 895.9 g.

| Ingredient | % by weight |
| --- | --- |
| NiL$_4$ | 0.00 |
| L:P(OPh)$_3$ | 1.13 |
| ZnCl$_2$ | 0.09 |
| BHC | 0.10 |
| NDC's | 97.81 |

| Ingredient | % by weight |
| --- | --- |
| HCN | 0.03 |
| Others (balance) | 0.84 |

Therefore, the yield of NDC's was 99.9%. Nitrogen gas was bubbled through the solution at a flow rate of 500 ml/min for one hour and the insoluble matter was filtered off.

The resulting filtrate was a crude NDC's solution, which was used in the following examples.

EXAMPLE 2

Treatment of Catalysts in Crude NDC's Solution 15 g of toluene and 50 g of the crude NDC's solution (98.48% by weight of NDC's) Obtained in Example 1 was placed in a 100 ml round-bottom flask fitted with a stirrer, a thermometer and a cooler, and 10.0 g of a 8 wt. % aqueous solution of sodium hydroxide was added thereto followed by heating with stirring at 5° C. for one hour. The resulting solution was transferred into a 300 ml separatory funnel and the NDC's were extracted with 85 g of toluene. The resulting mixture was allowed to stand and the mixture solution was separated into two phases. The lower liquid phase (water phase) was separated. Then 50 g of water was added to the remaining upper liquid phase (organic phase containing NDC's), an organic phase containing NDC's, shaked sufficiently and allowed to stand, and the resulting lower liquid phase (water phase) was separated. This water washing procedure was repeated three times.

After a series of the post treatments as mentioned above, 149.0 g of a solution of NDC's in toluene (containing 32.72% by weight of NDC's) was obtained. As a result, the Yield of NDC's in the procedure was 99.0%,

EXAMPLE 3

The procedure of Example 2 was repeated except that a 25 wt. % aqueous solution of sodium hydroxide was used in place of a 8 wt. % aqueous solution of sodium hydroxide (the weights of both solutions being the same) and the contacting time was changed to 20 min. The Yield of NDC's was 98.6% .

EXAMPLE 4

The procedure of Example 2 was repeated except that the temperature and the time contacting the aqueous solution of sodium hydroxide were changed to 60° C. and 0.5 hour, respectively. The yield of NDC's was 98.8% .

EXAMPLE 5

The procedure of Example 2 was repeated except that 21.4 g of a 8 wt. % aqueous solution of barium hydroxide was used in place of 10.0 g of a 8 wt. % aqueous solution of sodium hydroxide. The yield of NDC's was 98.7% .

EXAMPLE 6

The procedure of Example 2 was repeated except that 12.3 g of 8 wt. % sulfuric acid was used in place of 10.0 g of a 8 wt. % aqueous solution of sodium hydroxide. The yield of NDC's was 98.9% .

EXAMPLE 7

The procedure of Example 2 was repeated except that a 50 wt. % aqueous solution of acetic acid was used in place of a 8 wt. % aqueous solution of sodium hydroxide (the weights of both solutions being the same) and the contacting temperature and the contacting time were changed to 70° C. and 3 hours, respectively. The yield of NDC's was 98.2%.

EXAMPLE 8

The procedure of Example 2 was repeated except that 4.1 g of 3 wt % aqueous hydrogen peroxide was used in place 10.0% of a 8 wt. % aqueous solution of sodium hydroxide and the contacting temperature was changed to 20° C. The yield of NDC's was 98.5%.

EXAMPLE 9

The procedure of Example 2 was repeated except that 4.1 g of a 8% wt. % aqueous solution of t-butylhydroperoxide was used in place of 10.0 g of a 8 wt. % aqueous solution of sodium hydroxide and the contacting temperature was changed to 20° C. The yield of NDC's was 98.4%.

EXAMPLE 10

The procedure of Example 2 was repeated except that 18.2 g of a 5 wt. % aqueous solution of iodine-potassium iodide was used in place of 10.0 g of a 8 wt. % aqueous solution of sodium hydroxide and the contacting temperature was changed to 20 C. The yield of NDC's was 98.6%.

EXAMPLE 11

The procedure of Example 2 was repeated except that 0.03 g of 2,2'-azobis (isobutyronitrile) was used in place of 10.0 g of a 8 wt. % aqueous solution of sodium hydroxide and the contacting temperature and the contacting time were changed to 80° C. and 2 hours, respectively, and the contacting treatment was carried out in an oxygen atmosphere (oxygen being bubbled through the solution). The yield of NDC's was 98.0%.

EXAMPLE 12-21

Catalytic hydrogenation of NDC's solution after treating catalysts 50.0 g of each of 31-33 wt. % solution of NDC's obtained in Examples 2-11 in toluene and 0.16 g of a Raney cobalt catalyst were fed into a 100 ml autoclave and the resulting system was purged with nitrogen followed by pouring 3.6 g of liquid ammonia thereinto. Then hydrogen gas was pressed into the autoclave up to 70 kg/cm²G and the temperature was elevated with stirring. Further hydrogen gas was fed so as to keep the temperature at 150.C and the pressure at 60-100 kg/cm²G while a catalytic hydrogenation reaction was carried out for 2.5 hours.

As a result, the reaction involving each of the toluene solution of NDC's obtained in Examples 2-11 proceeded substantially quantitatively and the yield of BAN's in the catalytic hydrogenation reaction calculated based on the fed NDC's was in the range of 99.0 to 99.5%. The overall Yield of BAN's from BHC was in the range of 97 0 to 98.4%.

COMPARATIVE EXAMPLE 1

The procedure of Example 2 was repeated except that a 8 wt. % aqueous solution of sodium hydroxide gas replaced by the same amount of water. The yield of NDC's was 99.0%.

The resulting NDC's were used to effect a catalytic hydrogenation reaction following the procedure of Example 12. The resulting Yield of BAN's was 12.5% and the overall yield of BAN's from BHC was 12.4%.

COMPARATIVE EXAMPLE 2

The procedure of Comparative Example 1 was repeated except that 10.0 g of water was replaced by 30.0 g of water. The yield of NDC's was 98.8%.

The resulting NDC's were subjected to a catalytic hydrogenation reaction following the procedure of Example 12. The yield of BAN's was 14.7% and the overall yield of BAN's from BHC was 14.5%.

COMPARATIVE EXAMPLE 3

The procedure of Comparative Example 2 was repeated except that the contacting temperature and the contacting time were changed to 70 C and 3 hours, respectively. The Yield of NDC's was 98.7%.

The resulting NDC's were subjected to a catalytic hydrogenation reaction following the procedure of Example 12. As a result, the yield of BAN's gas 17.1% and the overall yield thereof from BHC was 16.9%.

COMPARATIVE EXAMPLE 4

The procedure of Example 2 was repeated except that 10.0 g of a 8 wt. % aqueous solution of sodium hydroxide was replaced by 7.8 g of a 15 wt. % aqueous solution of sodium chloride. The yield of NDC's was 99.2%.

The resulting NDC's were subjected to a catalytic hydrogenation reaction following the procedure of Example 12. The yield of BAN's was 8.3% and the overall yield thereof from BHC was 8.2%.

What is claimed is:

1. A process for producing a norcamphane dicarbonitrile of the formula (II):

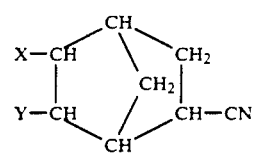

where X and Y are selected from the group consisting of hydrogen and cyano provided that X and Y are different, which comprises:

hydrocyanating bicyclo [2,2,1]-5-heptane-2-carbonitrile of the formula (I):

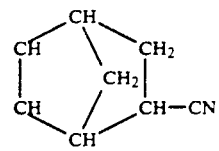

in the presence of a zerovalent nickel complex catalyst represented by the formula (III):

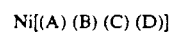

Ni[(A) (B) (C) (D)]    (III)

where A, B, C and D are, similar or dissimilar, neutral ligands of the formula (IV):

$$P_{(x)(y)(z)} \quad \text{(IV)}$$

where P is phosphorus atom, x, y and z are similar or dissimilar groups represented by OR where R is selected from the group consisting of alkyl having 18 carbon atoms or less and aryl having 18 carbon atoms or less; a neutral ligand of the formula (IV):

$$P_{(x)(y)(z)} \quad \text{(IV)}$$

where P is phosphorus atom and x, y and z are similar or dissimilar groups represented by OR where R is selected from the group consisting of alkyl having 18 carbon atoms or less and aryl having 18 carbon atoms or less; and a Lewis acid, in a liquid phase, and treating the resulting crude norcamphane carbodinitrile product fluid by contact with a catalyst treating agent which comprises an aqueous alkaline solution, an aqueous acidic solution or an oxidizing agent so as to hydrolyze or oxidize the catalyst, ligand and Lewis acid.

2. A process according to claim 1, further comprising washing the crude norcamphane carbodinitrile product with water after treatment by contact with the catalyst treating agent.

3. A process according to claim 2, further comprising adding a hydrophobic organic solvent in advance of washing with water.

4. A process according to claim 1, wherein the Lewis acid is a compound composed of an anion and a metal cation of an element selected from the group consisting of Groups IIa, IIIa, IVa, Va, VIa, VIIa, VIII, Ib, IIb, IIIb, and IVb of the Periodic Table.

5. A process according to claim 1, wherein the aqueous alkaline solution comprises an aqueous solution of an alkaline metal hydroxide, an aqueous solution of an alkaline earth metal hydroxide, an aqueous solution of an alkaline metal carbonate or aqueous ammonia.

6. A process according to claim 1, wherein the aqueous acidic solution comprises an aqueous solution of mineral acids or carboxylic acids.

7. A process according to claim 1, wherein the oxidizing agent comprises hydrogen peroxide, organic peroxides, organic peracids, sulfoxides, halogen, halogen compounds, ozone, nitrogen oxides, epoxides, amine N-oxides or oxygen.

8. A process according to claim 3, wherein the hydrophobic organic solvent comprises aromatic hydrocarbons, aromatic halogenated hydrocarbons, aliphatic ethers, aliphatic halogenated hydrocarbons, aliphatic alcohols having 4 carbon atoms or more, aliphatic carboxylic acid esters, or mixtures thereof.

* * * * *

UNITED STATES PATENT AND TRADEMARK OFFICE
CERTIFICATE OF CORRECTION

PATENT NO. : 5,087,722
DATED : February 11, 1992
INVENTOR(S) : Inomata et al It is certified that error appears in the above-identified patent and that said Letters Patent is hereby corrected as shown below:

In column 12, lines 55-59, please deelte Formula I and insert new Formula I:

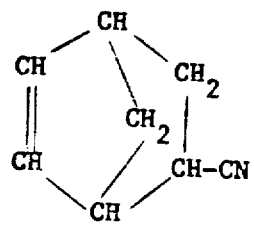

Signed and Sealed this

Twentieth Day of July, 1993

Attest:

MICHAEL K. KIRK

Attesting Officer

Acting Commissioner of Patents and Trademarks